United States Patent [19]

Barker et al.

[11] 4,177,259

[45] Dec. 4, 1979

[54] WATERPROOF MAKEUP AND METHOD OF PREPARING SAME

[75] Inventors: Graham Barker, Fair Lawn; Martin J. Barabash, Montvale, both of N.J.

[73] Assignee: Witco Chemical Corporation, New York, N.Y.

[21] Appl. No.: 815,477

[22] Filed: Jul. 14, 1977

[51] Int. Cl.$^2$ ............................................... A61K 7/021
[52] U.S. Cl. ........................................................ 424/63
[58] Field of Search .................. 424/63, 365, 170, 172

[56] References Cited

U.S. PATENT DOCUMENTS

| | | |
|---|---|---|
| 2,294,233 | 8/1942 | Harris .................................... 424/365 |
| 3,266,995 | 8/1966 | Lanzet et al. ........................... 424/63 |
| 3,536,816 | 10/1970 | Kellner .................................. 424/365 |
| 3,926,840 | 12/1975 | Wendler et al. ................... 424/172 X |
| 3,957,969 | 5/1976 | Fujiyama et al. ................. 424/365 X |

*Primary Examiner*—Albert T. Meyers
*Assistant Examiner*—H. Steven Seifert
*Attorney, Agent, or Firm*—Albert L. Gazzola; Morton Friedman

[57] ABSTRACT

A method of making a water-in-oil waterproof makeup comprising (a) a cosmetic emulsion oil, (b) a cosmetic pigment, and (c) an emulsifier combination comprising (i) a stearate and (ii) a polyhydric alcohol ester of a liquid fatty acid, and compositions therefrom.

8 Claims, No Drawings

WATERPROOF MAKEUP AND METHOD OF PREPARING SAME

BACKGROUND

The science of emulsions and the techniques of emulsification are replete with analyses and theories representing continuing efforts to determine the true nature of oil-in-water emulsions (O/W) and water-in-oil emulsions (W/O). The true nature of emulsions involves, inter alia, (i) surface chemistry, e.g., the interfacial tension between the so-called disperse and the continuous phases, (ii) the physical properties of emulsions, including emulsion stability and the tendency to demulsify, to invert, to cream, (iii) the sensitive and very critical function of emulsifying agents, (iv) and the like.

Any number of equations and tables have been derived over the years as researchers persevere in their attempts, for example, to relate the viscosity of an emulsion to the viscosity of its continuous phase, and/or to the concentration of its internal phase, and/or to the interfacial film provided by emulsifying agents, and/or to the type of emulsifier and concentration thereof. Of course, the recondite principles inherent in electrophoretic studies of emulsions dramatically illustrate the quest for insight into the enigmatic entity known as an emulsion.

A well-respected emulsion textbook author, Paul Becher, expresses it better when he admits:

"... emulsion theory has progressed to a point where some sort of theoretical interpretation of emulsion behavior is possible; the prediction of emulsion behavior is still largely a matter of art rather than science." (Emphasis added)[1]

[1] Becher, "Emulsions: Theory and Practice," (1957), page 85, American Chemical Society Monograph Series. Reinhold Publishing Corporations, NY.

Typically, while Becher reports that early on it was found that the emulsifying agents "... sodium, potassium and lithium soaps ... give O/W emulsions ... [and] magnesium, strontium, barium, iron and aluminum soaps give W/O emulsions ... ",[2] he is quick to qualify predictability throughout his text when reporting on research findings using mixtures of emulsifying agents, varied concentrations of emulsifying agents, varied internal phase ratios, and the like.

[2] Idem, page 86; idem, cf. also page 88.

Another illustration in this vein is the author's discourse on the hydrophilic/lipophilic (polar/non-polar) characteristics of molecules. A linear $C_{12}$ hydrocarbon, for example, terminated at one end with a polar (water-soluble) moiety, such as a carboxy group or its lower alkyl ester, is said to be amphiphilic, i.e., one end of the hydrocarbon is soluble in water and the other end is more soluble in non-polar organic solvents, such as benzene. From these observed characteristics there evolved over the years a method of selecting emulsifiers (surface active agents) on the basis of their so-called hydrophile/lipophile balance (HLB).[3] Unfortunately, as Becher and others are quick to point out, experiences with emulsions reported throughout the literature reveal that the HLB method has by no means obviated the need for trail and error.

[3] See "Emulsions & Emulsion Science", Lissant, Vol. II, pages 734-743, for a dissertation by Charles Fox on HLB values.

The following U.S. patents by Benjamin R. Harris, taken in conjunction with the Becher text, cited supra (footnote 1), give further insight (practical) into the hydrophile/lipophile properties of emulsifying agents used to form W/O emulsions:

U.S. Pat. No. 2,109,842; issued Mar. 1, 1938
U.S. Pat. No. 2,114,490; issued Apr. 19, 1938
U.S. Pat. No. 2,177,983; issued Oct. 31, 1939
U.S. Pat. No. 2,294,233; issued Aug. 25, 1942

The patents were uncovered in a recent study of the patent literature. In addition, the following patents were found:

| Patentee/s | Country | U.S. Pat. No. | Issued |
|---|---|---|---|
| Schanzle et al. | U.S. | 2,091,886 | 8/31/37 |
| Muller et al. | U.S. | 2,350,800 | 6/6/44 |
| Nichols et al. | U.S. | 2,695,877 | 11/30/54 |
| Telle et al. | U.S. | 3,127,311 | 3/31/64 |
| Pader et al. | U.S. | 3,248,229 | 4/26/66 |
| Lachampt et al. | U.S. | 3,846,546 | 11/5/74 |
| Viout et al. | U.S. | 3,860,700 | 1/14/75 |
| Meguro et al. | U.S. | 3,875,196 | 4/1/75 |
| Lissant | U.S. | 3,892,881 | 7/1/75 |
| Thomas | U.S. | 3,929,499 | 12/31/75 |
| Johnson | U.K. | 417,715 | 10/1/34 |

Broadly speaking, careful study of each of these references shows that they are readily distinguishable from the present claimed discovery and they neither implicitily or explicitly suggest same. This will become even more apparent from the more detailed description hereinbelow of the claimed invention.

The transition from emulsion art to emulsion science, so to speak, is an arduous experience; it records and portends a path strewn with shattered predictions. Witness the oldest emulsions, viz., cosmetic emulsions, the preparation of which has traditionally been an art. Success has been consequent on trial and error and the judgment and good fortune of the "cosmeticulous." Only fairly recently, according to Becher, supra, can "... broad generalizations ... be made which will guide the unintiated." (Emphasis added).[4]

[4] Cf. Ftn: 1, supra, page 245 thereof.

It will be shown, infra, that the present discovery advances the art in a way which inherently flies in the teeth of present-day scientific, albeit somewhat eclectic, rationale. Typical of findings leading to this rationale are those reported in the periodical, "Norda Schimmel", No. 430, pages 1-3, April 1971, published by Norda/Schimmel International, New York, NY in which it is pointed out that:

"Emulsions of the water-in-oil type generally are not as stable as emulsions having water as the continuous phase. One reason is that the viscosity of the external phase changes with temperature." (Idem. page 1, col. 2)

It is further noted that when calcium stearate or aluminum stearate is used as the emulsifying agent it is best formed "in situ." (Idem, page 1, column 1, and page 2, columns 1 and 2, respectively.)

According to the periodical, also, calcium stearate is "insoluble in mineral oil as well as in water, but ... sparingly soluble in mineral oil on heating." (Idem, page 1, column 1.)

Aluminum stearate, on the other hand, is much more soluble in fatty oils and mineral oil" than calcium stearate:

"When 5 percent of aluminum stearate is stirred into mineral oil, the powder partially dissolves at room temperature, and on heating the solution becomes clear. At around 100° C. the solution becomes highly viscous, behaving like a dispersion of a water-soluble gum in water. On cooling, the solution sets to a gel which is not very stable. Aluminum stearate is useful in W/O emulsions not only for its emulsifying activity but because it thickens or gels the oil phase. The high viscosity of the external phase helps to prevent coalescence of the water droplets and creaming of the emulsion." (Emphasis added) Idem, see paragraph bridging part 1, column 2 and page 2, column 1 of the periodical.

INVENTION

This invention relates to waterproof makeup having a disperse phase and an oil-pigment phase. More particularly, the instant discovery concerns a waterproof makeup which comprises (a) a cosmetic emulsion oil, (b) a cosmetic pigment, (c) an emulsifier combination comprising an aluminum and/or calcium stearate and a polyhydric alcohol ester of a liquid fatty acid having an HLB value of less than 5, and (d) water.

Unlike conventional makeup preparations, and as indicated above, the makeup is waterproof. In other words, when rubbed gently on the skin or blended into the surface of the skin in the usual manner (this is known as "playtime"), it leaves a much softer, more elegant feel on the skin, it does not cake or crack. Furthermore, it takes longer for the drying process, thus allowing the user greater freedom in blending and application (again, "playtime").

Conventional makeups are oil-in-water compositions of emulsion oils, pigments and emollients dispersed in an aqueous medium. Characteristically, these conventional makeups tend to cake both on application and, as any user has observed, on, for example, the inner surfaces of the bottle container neck and cap as well as on the lip of the bottle opening.

It has been found that unlike conventional makeups which are sensitive to water, the makeups of the present invention are waterproof. A simple and dramatic test illustrating this fact can be carried out by applying a small amount of a conventional makeup to the back of one hand and, to the back of the other hand, applying the same amount of makeup of the present invention. About 8 or 10 droplets of water superimposed on the film of the waterproof makeup of the present invention will bead and roll off; it won't penetrate. Not so, however, when a similar amount of water is superimposed on the film of conventional makeup on the back of the other hand. Due to the hydrophilic nature of the water-pigment phase of the latter, the droplets of water blend with the makeup and do not bead and roll off.

Of course, the advantages of a waterproof makeup are innumerable, since there is no drying tendency as in the case of the well-known commercial preparations; the waterproof makeup has good moisturizing and skin softening properties; it has less drying effect on the skin; and it has other like distinctive and inherent properties.

Advantages in preparation are likewise significant. Minimal effort is needed to get a uniform dispersion of the pigments in the oil medium, unlike the case of water-pigment dispersions. No milling or grinding is necessary.

Repeating, the present invention concerns water-in-oil type emulsion compositions having an oleaginous-pigmented phase and a discontinuous (internal or disperse) aqueous phase. These compositions comprise, pursuant to the instant discovery, (a) a cosmetic emulsion oil, (b) a cosmetic pigment, (c) an emulsifier combination comprising an aluminum and/or calcium stearate and a polyhydric alcohol ester of a liquid fatty acid having an HLB value of less than 5, and (d) water.

Typical cosmetic emulsion oils suitable for the present invention are the following:

mineral and/or other hydrocarbon oils, such as squalene, squalane, and the like;

fatty alcohol esters, such as stearyl alcohol esters of $C_{12}$–$C_{18}$ fatty acids, isostearyl alcohol esters of $C_{12}$–$C_{18}$ fatty acids, oleyl alcohol esters of $C_{12}$–$C_{18}$ fatty acids;

waxes, such as beeswax, spermaceti, paraffin, petrolatum;

synthetic waxes, such as hydroxyethyl stearamide, cetyl stearate, stearic diethanolamide, and other like well-known cosmetic emulsion waxes.

Additional illustrations may be found throughout the art, e.g., cf. patents above cited.

As to the concentration of cosmetic emulsion oil in the compositions of the present invention, a quantity sufficient is added to provide the balance of components up to 100%.

Typical cosmetic pigments within the purview of the present invention are finely-divided oil-dispersible $TiO_2$; low micron number; hydrophobic, cosmetic yellow and red iron oxide; hydrophobic ultramarine blue, rose, green, pink, red and violet; mica; aluminum powder; guanine; bismuth oxychloride; chromium hydroxide green; chromium oxide greens, copper metallic powder; ferric ferrocyanide (iron blue); quanine (pearl essence); manganese violet; and the like. The particle size of these pigments is in the range of about 0.5 micron to about 3 micron, preferably about 0.3 micron to about 1.5 micron. The concentration thereof is in the range of about 2 to about 20 percent by weight, preferably 8–12 percent by weight, based upon the total concentration of the makeup composition.

As to the aluminum and/or calcium stearate co-emulsifier, aluminum stearate is preferred. The concentration of said metal stearate/s employed in the emulsions of the present invention is in the range of about 0.5 to about 3.0 percent by weight, preferably about 1 to about 2.5 percent by weight, of the total weight of the emulsion.

The polyhydric alcohol ester is present in the concentration of about 0.6 to about 3.6, preferably about 1.5 to about 3.0, based upon the total weight of the makeup composition.

It is a significant advantage of the instant discovery that up to about 85 percent water may be present as the disperse phase, based upon the total weight of the W/O emulsion. Generally from about 40 to about 85 percent water is present, preferably about 50 to about 78 percent.

Incorporation of conventional minor amounts of likewise conventional cosmetic emulsion additives is within the purview of the present invention. For example, up to about 0.5% by weight, based upon the total weight of the emulsion, of a preservative may be present in the claimed composition without modifying the basic nature of same. Similarly, fragrance and color can be added for aesthetic purposes.

According to a preferred emodiment, the emulsifier combination, pigment, and oil are pre-blended at an elevated temperature with stirring; water preheated to about the same temperature is then mixed in with oil/-pigment emulsifier blend. It has been found that temperatures in the range of about 90° C. to about 95° C. are required, preferably using mild agitation over a period of a few minutes to an hour, or until the aluminum stearate, say, is adequately dispersed, to effect the high internal phase ratio water-in-oil emulsions of the present invention. More intense agitation may be employed, however, to produce the emulsions herein contemplated.

EXAMPLES

The present invention will better be understood from the following examples which are intended to be illustrative only, i.e., not unduly limitative (unless otherwise indicated percentages and parts recited in the examples are by weight):

EXAMPLE I

|  | % W/W |
|---|---|
| Oil Phase | |
| Witconol 14 [Polyglycerol (4) monooleate] | 3.0 |
| Aluminum Stearate | 1.5 |
| Aristowax 143 [Paraffin Wax (143° F. m.p.)] | 5.0 |
| Mineral Oil (70 sus visc.) | 23.5 |
| Pigment Blend (cf. infra.) | 8.0 |
| Water Phase | |
| Germall 115 (imidazolidinyl urea) | 0.25 |
| Methyl Paraben USP (methyl para-hydroxy benzoate) | 0.15 |
| Propyl Paraben USP (propyl para-hydroxy benzoate) | 0.10 |
| Deionized Water | 58.5 |
| Pigment Blend | |
| Oil Dispersible TiO$_2$ | 87.8 |
| Low Micron Umber | 5.2 |
| Cosmetic Yellow Iron Oxide | 5.2 |
| Cosmetic Red Iron Oxide | 1.8 |

Procedure: Hot oil phase, sans pigment, to 90°–95° C. and stir 10–15 minutes. Disperse premixed pigment blend in hot oil phase and stir for 15 minutes. Heat water phase to 90°–95° C. When preservatives are dissolved, add water phase (at 90°–95° C.) to oil phase with moderate agitation while maintaining temperature at 90°–95° C. When all the water phase has been added continue stirring and maintain temperature for additional 15–30 minutes. Then, let cool with stirring and package at 28° C. in containers. Cooling period is 3 hours.

Composition (emulsion) is stable at 45° C. for 30 days. No separation after 3 freeze/thaw cycles.

EXAMPLE II

Example I is repeated in every essential respect, but at 28° C. emulsion is stirred on Greer Homomixer for 10 minutes at approximately 1500–2000 rpm. Emulsion after 31 days at 45° C. shows good emulsion stability and exhibits no pigment flooding. After 3 freeze/thaw cycles the emulsion is stable.

EXAMPLE III

|  | % W/W |
|---|---|
| Oil Phase | |
| Witconol 14 [Polyglycerol (4) monooleate] | 2.73 |
| Aluminum Stearate | 1.36 |
| Centrolene S (Lecithin) | 1.82 |
| Aristowax 143 [paraffin wax (243° F., m.p.)] | 4.55 |
| Mineral Oil | 19.55 |
| Pigment Blend (cf. infra) | 7.27 |
| Water Phase | |
| Germall 115 (cf. Example I) | 0.25 |
| Methyl Paraben USP (cf. Example I) | 0.15 |
| Propyl Paraben USP (cf. Example I) | 0.1 |
| Deionized Water | 62.2 |
| Pigment Blend | |
| Oil Dispersible TiO$_2$ | 87.1 |
| Low Micron Umber | 5.5 |
| Cosmetic Yellow Iron Oxide | 5.5 |
| Cosmetic Red Iron Oxide | 1.9 |

Procedure: Example I, supra, is repeated in every essential respect, except that the pigments are added to the oil phase, one at a time, and the cooling period is 2½ hours. Emulsion is stable through 3 freeze/thaw cycles. It is stable at 45° C. for 30 days.

EXAMPLE IV

Example III is repeated in every essential respect, except emulsion is stirred on a Gifford-Wood Homomixer for 10 minutes as in Example II, above. The resulting emulsion has the same stability properties as that of Example III, supra.

EXAMPLE V

|  | % W/W |
|---|---|
| Oil Phase | |
| Witconol GMOP (glycerol monooleate) | 3.0 |
| Aluminum Stearate | 1.5 |
| Mineral Oil | 16.5 |
| Petrolatum USP | 3.0 |
| Aristowax 143 [Paraffin Wax (243° F., m.p.)] | 3.0 |
| Witconol APS [polypropoxy 11 stearyl ether] | 3.0 |
| Pigments (same as in Example III, above) | 8.0 |
| Water Phase | |
| Germall 115 | 0.25 |
| Methyl Paraben USP | 0.25 |
| Propyl Paraben USP | 0.1 |
| Deionized Water | 61.5 |

Procedure: Example III is repeated in every essential respect, but cooling time is 3 hours and emulsion is packaged at 27° C.

EXAMPLE VI

Example V is repeated in every essential respect, but aluminum stearate was omitted from the emulsion.

A bad paraffin separation was observed after 10 days at elevated temperature (45° C.). The emulsion completed 1 freeze/thaw cycle and broke during the second cycle.

EXAMPLE VII

|  | % W/W |
|---|---|
| Oil Phase | |
| Emsorb 2502 (Sorbitan Sesquioleate) | 3.0 |
| Aluminum Stearate | 1.5 |
| Mineral Oil | 16.5 |
| Petrolatum USP | 3.0 |
| Aristowax 143 [Paraffin wax(143° F. m.p.)] | 3.0 |
| Witconol APS [polypropoxy 11 stearyl ether ] | 3.0 |
| Pigments (same as Example III, above) | 8.0 |
| Water Phase | |
| Germall 115 | 0.25 |
| Methyl Paraben USP | 0.15 |
| Propyl Paraben USP | 0.1 |
| Deionized Water | 61.5 |

Procedure: Example III is repeated in every essential respect, but emulsion is packaged at 29° C. after 4½ hours of cooling.

EXAMPLE VIII

Preparation is the same as Example VII, above, except aluminum stearate is omitted.

Emulsion developed a bad paraffin separation after 10 days in 45° C. oven and had no freeze/thaw stability.

EXAMPLE IX

| | % WW |
|---|---|
| Oil Phase | |
| Witconol 14 (see Example I, supra.) | 3.0 |
| Aluminum Stearate | 1.5 |
| Aristowax 143 [paraffin wax (143° F., m.p.) | 5.0 |
| Carnation Mineral Oil | 23.5 |
| Pigment Blend (cf. infra.) | 8.0 |
| Water Phase | |
| Germall 11 | 0.25 |
| Methyl Paraben USP | 0.15 |
| Propyl Paraben USP | 0.10 |
| Deionized Water | 58.5 |
| Pigment Blend | |
| Oil Dispersible TiO$_2$ | 69.1 |
| Hydrophobic Ultramarine Blue | 23.9 |
| Hydrophobic Ultramarine Rose | |
| (Mixed and ground in a Waring Blender) | 7.0 |

Procedure: Emulsion was prepared as in Example I, above, except it was cooled for 3 hours to 29° C., and packaged.

Emulsion has good stability at 45° C. and completed 3 freeze/thaw cycles.

EXAMPLE X

Same as Example IX, above, except emulsion was stirred for 10 minutes on Gifford-Wood Homomixer.

Stability is the same as Example IX.

EXAMPLE XI

| | % W/W |
|---|---|
| Oil Phase | |
| Witconol 14 [polyglycerol (4) monooleate] | 3.0 |
| Calcium Stearate | 1.5 |
| Mineral Oil | 4.1 |
| Isopropyl myristate | 12.4 |
| Petrolatum USP | 3.0 |
| Aristowax 143 [paraffin wax (143° F., m.p.)] | 3.0 |
| Witconol APS [polypropoxy (11) stearyl ether] | 3.0 |
| Water Phase | |
| Germall 115 | 0.25 |
| Methyl Paraben USP | 0.15 |
| Propyl Paraben USP | 0.1 |
| Deionized Water | 61.5 |
| Pigment Blend | |
| Oil dispersible TiO$_2$ | 87.0 |
| Cosmetic yellow iron oxide-hydrophobic | 5.5 |
| Cosmetic red iron oxide-hydrophobic | 2.0 |
| Cosmetic umber iron oxide hydrophobic | 5.5 |

Procedure: Example III, above, is repeated in every essential respect, but the resulting emulsion cooled from 90° to 35° C. in 1½ hours and then to 29° C. in 1½ hours.

Emulsions has good freeze/thaw stability. Emulsion when stored in plastic containers at 45° C. is good.

EXAMPLE XII

Example XI is repeated in every essential respect, but the emulsions are stirred on a Homomixer for 10 minutes at 29° C. and packaged.

Emulsion had good freeze/thaw stability and is stable at 45° C. in plastic and glass.

Pursuant to statutory requirements, there are described above the invention and what are now considered its best embodiments. It should be understood, however, that the invention can be practiced otherwise than as specifically described within the scope of the appended claims.

What is claimed:

1. A method of preparing a stable waterproof makeup having a water disperse phase and an oil continuous phase which comprises (A) admixing (a) a cosmetic emulsion oil and (b) a cosmetic pigment and (c) an emulsifier combination comprising (i) a stearate selected from the group consisting of aluminum stearate, calcium stearate and mixtures thereof, and (ii) a polyhydric alcohol ester of a liquid fatty acid having an HLB value less than 5 and selected from the group consisting of polyglycerol (4) monooleate, sorbitan sesquioleate and glycerol monooleate; and (B), while agitating, blending at 90° C.–95° C. therewith (d) water which has been heated to a temperature in the range of about 90° C. to about 95° C.

2. The method of claim 1 wherein components (a), (b), (c) and (d) are present in the following concentration ranges expressed in percent by weight based upon the total weight of the emulsion:

| Component | Concentration Range |
|---|---|
| (a) Cosmetic emulsion oil | balance |
| (b) Cosmetic pigment | 2–20 |
| (c) Emulsifier combination of Claim 7: | |
| (i) Stearate | 0.5–3.0 |
| (ii) Polyhydric alcohol ester | 0.6–3.6 |
| (d) H$_2$O | 40.0–85.0 |

3. The stable waterproof makeup prepared by the method of claim 1.

4. The stable waterproof makeup prepared by the method of claim 2.

5. The emulsion of claim 4 wherein concentration ranges are:

| Component | Concentration Range |
|---|---|
| (a) Cosmetic emulsion oil | balance |
| (b) Cosmetic pigment | 8–12 |
| (c) Emulsifier combination of Claim 2: | |
| (i) Stearate | 1.0–2.5 |
| (ii) Polyhydric alcohol ester | 1.5–3.0 |
| (d) H$_2$O | 50.0–78.0 |

6. The emulsion of claim 4 where in the polyhydric alcohol ester co-emulsifier is polyglycerol (4) monooleate.

7. The emulsion of claim 4 wherein the polyhydric alcohol ester co-emulsifier is sorbitan sesquioleate.

8. The emulsion of claim 4 wherein the polyhydric alcohol ester co-emulsifier is glycerol monooleate.

* * * * *